(12) United States Patent
Bianchi et al.

(10) Patent No.: US 8,257,308 B2
(45) Date of Patent: Sep. 4, 2012

(54) DRUG DELIVERY DEVICE WITH A MODULE FOR PREVENTING FIBRILLATION DOWNSTREAM OF ITS RESERVOIR

(75) Inventors: François Bianchi, Martigny (CH); Christophe Conan, Ferney-Voltaire (FR)

(73) Assignee: Debiotech S.A., Lausanne (CH)

(*) Notice: Subject to any disclaimer, the term of this patent is extended or adjusted under 35 U.S.C. 154(b) by 0 days.

(21) Appl. No.: 13/059,516

(22) PCT Filed: Jul. 20, 2009

(86) PCT No.: PCT/IB2009/053128
§ 371 (c)(1), (2), (4) Date: Feb. 17, 2011

(87) PCT Pub. No.: WO2010/023567
PCT Pub. Date: Mar. 4, 2010

(65) Prior Publication Data
US 2011/0144585 A1    Jun. 16, 2011

(30) Foreign Application Priority Data
Aug. 25, 2008  (EP) .................................... 08162871

(51) Int. Cl.
*A61M 1/00*    (2006.01)

(52) U.S. Cl. .................................................. 604/126

(58) Field of Classification Search .................. 604/122, 604/126
See application file for complete search history.

(56) References Cited

U.S. PATENT DOCUMENTS

| 4,642,098 A * | 2/1987 | Lundquist ..................... 604/123 |
| 5,417,663 A * | 5/1995 | Slettenmark .................. 604/126 |
| 6,632,217 B2 * | 10/2003 | Harper et al. ............... 604/892.1 |
| 2002/0193732 A1 | 12/2002 | Naimark et al. |
| 2005/0287515 A1 | 12/2005 | Deppisch et al. |
| 2007/0255237 A1 | 11/2007 | Lobl et al. |

FOREIGN PATENT DOCUMENTS

| EP | 1 283 051 B1 | 6/2006 |
| WO | WO 02/085428 | 10/2002 |
| WO | WO 03/002141 | 1/2003 |

OTHER PUBLICATIONS

International Search Report for PCT/IB2009/03128, mailed Nov. 26, 2009.
Written Opinion of the International Searching Authority for PCT/IB2009/03128, mailed Nov. 26, 2009.
Nielsen et al, Effect of Environmental Factors on the Kinetics of insulin Fibril Formation: Elucidation of the Molecular Mechanism, Biochemistry, vol. 40 (2001), pp. 6036-6046.

* cited by examiner

*Primary Examiner* — Christopher D Koharski
*Assistant Examiner* — Diva K Chander
(74) *Attorney, Agent, or Firm* — Nixon & Vanderhye P.C.

(57) ABSTRACT

The invention relates to a drug delivery device (1, 100), in particular for the delivery of drugs comprising molecules tending to spontaneously form nucleation seeds leading to fibrils, comprising a drug reservoir (2, 102) having a reservoir outlet (107) connected to a device outlet, adapted to deliver a drug fluid to a patient's body, through a pathway (5) including a fluid flow controlling system (4, 104). The pathway further includes a filtration module (6, 106) adapted to retain the nucleation seeds, preferably by forcing them through a filtering membrane pores and on the basis of hydrophobic interaction with the membrane.

18 Claims, 4 Drawing Sheets

DRUG DELIVERY DEVICE WITH A MODULE FOR PREVENTING FIBRILLATION DOWNSTREAM OF ITS RESERVOIR

This application is the U.S. national phase of International Application No. PCT/IB2009/053128 filed 20 Jul. 2009, which designated the U.S. and claims priority to Europe Application No. 08162871.1 filed 25 Aug. 2008, the entire contents of each of which are hereby incorporated by reference.

TECHNICAL FIELD

The present invention relates to a drug delivery device, in particular for the delivery of drugs comprising molecules tending to spontaneously form nucleation seeds leading to fibrils and aggregates, comprising a drug reservoir having a reservoir outlet connected to a device outlet, adapted to deliver a drug fluid to a patient's body, through a pathway including a fluid flow controlling system.

More precisely, the delivery device according to the invention is particularly well adapted for the delivery of insulin.

BACKGROUND ART

The neutral insulin solution introduced as Actrapid (registered trademark) nearly 40 years ago can be stored for several years at room temperature without significant change or loss of biological activity.

However, many investigators working with continuous insulin infusion from delivery device have noted the progressive propensity of insulin in solution to aggregate and form precipitate. Therefore, this inherent tendency of insulin to form aggregate or fibrils by non-covalent polymerization, which is promoted by a combination of physical factors, such as heat, movement, and hydrophobic surfaces, presents a major impediment to safe clinical application of insulin drug delivery systems.

Many different ways of increasing the physical stability of insulin for use in infusion pump have been reported. These methods include the use of organic medium, the introduction of organic and inorganic additives, and the use of insulin derivates.

Only a few of these methods are effective without compromising the quality of insulin preparation. For example the addition of two extra $Zn^{2+}$ per hexamer of insulin has demonstrated an improved physical stability without affecting the chemical stability of the corresponding insulin solution.

Insulin fibril formation involves the dissociation of native associated states (hexamer, tetramer, and dimer) to give native monomer. Therefore, by stabilizing the hexamer insulin with two extra $Zn^{2+}$, the formation of the intermediate which then oligomerizes to form transient soluble oligomers that lead to a fibril nucleus will be strongly reduced resulting in an improved stability, i.e. a longer fibrillation lag time.

However, it has been reported that the addition of 0.5% fibril seeds to a fresh insulin solution results in a 10-fold decrease in the lag time and addition of fibril seeds at concentrations of 1, 5, and 10% relative to the concentration of the native insulin completely eliminated the lag phase.

These results demonstrate the dramatic effect of seeding on the lag time which is directly related to the length of time it takes to form the fibril nucleation.

The methods which have been disclosed so far, to improve physical stability of insulin solution in infusion system, have been focused on the preparation of new insulin formulations improving the physical stability of the insulin when exposed to high mechanical stress or high temperature.

They more particularly aim at improving delivery of insulin with continuous infusion devices which comprise a reservoir filled with the drug to be delivered to a patient and connected to the patient's body. Such devices are usually attached to the patient's body to be operative several days, while the reservoir may eventually be refilled periodically. Thus, the patient's body heat and the patient's motions create flow movements in the reservoir as well as in the tubing and pump of the device imparting a high amount of thermomechanical energy to the drug solution.

Prior art proposals to improve physical stability of insulin solutions are discussed in patent EP 1 283 051 B1, in which further stable insulin formulations are disclosed. However, such stabilized formulations do not completely address the potential risk of limited compatibility of the tubing and of the pump material with the insulin for long duration exposition, more especially when the infusion device has small dimensions, i.e. when it is a micro-device.

Indeed, a continuous exposure to condition simulating insulin infusion, in particular, is expected to accelerate the fibrillation process.

In a drug infusion system, the solution may reside in the reservoir for several days, which will promote fibril seeds formation, even with the above-mentioned stabilized formulations. If the amount of these fibrils is not an issue in term of insulin stability, the presence of these seeds represents a real problem for the functionality of the infusion system when the solution enters downstream of the fluidic path.

In fact, seeding a solution with preformed insulin aggregates markedly accelerates the rate of aggregate, which can alter some functionality of the device downstream of the reservoir such as the leaktightness of the system or the fluidic resistance of a channel or also modify the efficacy of the insulin itself.

This is particularly relevant if the fibrillation mechanism is promoted downstream of the reservoir by environmental conditions such as reservoir material, gas bubbles, temperature or shear forces. Therefore, the prevention of fibrillation in a device remains an important challenge to address.

DISCLOSURE OF THE INVENTION

A principal object of the present invention is to offset the drawbacks of the prior art mentioned above by avoiding the nucleation seeds to enter downstream of the reservoir, i.e. where the environmental condition can potentially favor fibrillation.

To that end, embodiments of the present invention include in particular a drug delivery device as disclosed above, characterised by the fact that the device pathway further includes a filtration module comprising a porous membrane which is adapted to absorb nucleation seeds.

According to a preferred embodiment, the filtration module is arranged at the reservoir outlet and may include a porous membrane.

More specifically, when the device is intended for delivery of insulin or any other drug having similar physicochemical properties, it may be further characterised by the fact that, either it has a mean pore size that is approximately X times the mean diameter of said nucleation seeds, where X is equal to 0.9, or smaller, in order to retain said nucleation seeds essentially by size screening, or it has a mean pore size that is approximately X times the mean diameter of said nucleus seeds, where X is equal to 2, or larger, in order to retain said nucleation seeds essentially by adsorption on the surface of the pores.

Indeed, the filtration module may exhibit hydrophobic surface properties in the second case. Thus, the principle of such a filtration module may be based on the hydrophobic nature of the nucleation seeds: in fact, the blockage of the seeds may be ensured by their adsorption on the filtration module surface.

In both cases, the filtration module may exhibit hydrophilic surface properties, at least at its external surface arranged on the reservoir side, so as to prevent air bubbles to travel in the pathway, outside the reservoir.

According to preferred features of the invention, the filtration module may comprise a porous membrane which may have a mean pore size in the range between 4 and 25 nm, for size screening or, alternately in the range between 50 and 1000 nm for filtration by adsorption.

The membrane may be made of a material taken from the group comprising: Polypropylene (PP), Polystyrene (PS), High impact polystyrene (HIPS), Acrylonitrile butadiene styrene (ABS), Polyethylene terephthalate (PET), Polyester (PES), Polyamides (PA) (Nylons), Poly(vinyl chloride) (PVC), Polyurethanes (PU), Polycarbonate (PC), Polyvinylidene chloride (PVDC), Polyethylene (PE), Polycarbonate/Acrylonitrile Butadiene Styrene (PC/ABS), Polymethyl methacrylate (PMMA), Polytetrafluoroethylene (PTFE), Polyetheretherketone (PEEK), Polyetherimide (PEI), Phenolics (PF), Urea-formaldehyde (UF), Melamine formaldehyde (MF), Polylactic acid and Plastarch material.

BRIEF DESCRIPTION OF THE DRAWINGS

Other characteristics and advantages of the present invention will become more clearly apparent on reading the following detailed description of a preferred embodiment, given with reference to the appended drawings that are provided by way of non-limiting examples, and in which.

MODE(S) FOR CARRYING OUT THE INVENTION

Figure 1:
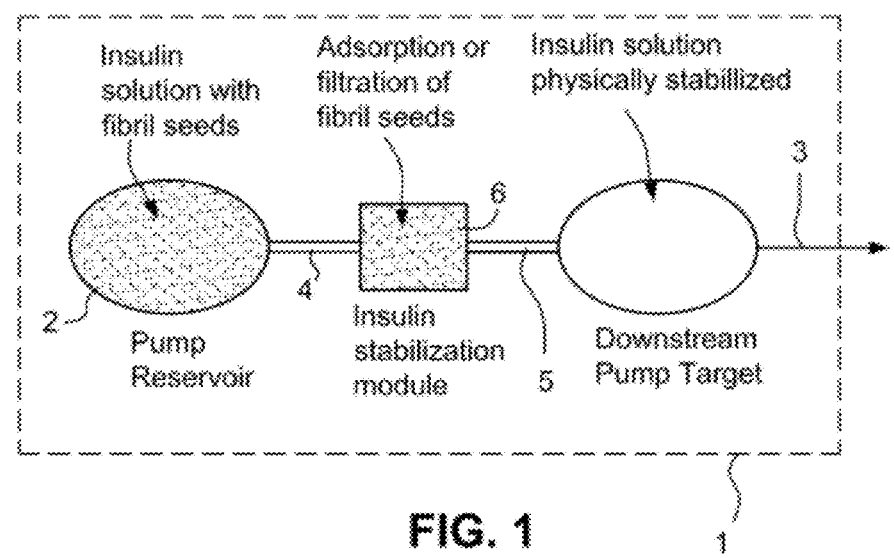
FIG. 1 shows a schematic diagram of a drug delivery device according to the present invention.

FIG. 1 shows a schematic diagram illustrating the principle of a drug delivery device according to the present invention.

It is proposed a drug delivery device 1 arranged for delivering drug from a drug reservoir 2 to a patient's body (illustrated by arrow 3 on FIG. 1) by means of a flow controlling system such as a pump 4 forcing the drug to circulate through a pathway including a tubing 5.

The device according to the invention further includes a filtration module 6 designed for preventing fibril seeds formed in the reservoir to enter downstream in the pathway, where a potential fibril agglomeration may present a real issue for the delivery device or for the drug.

Advantageously, the filtration module may comprise a filter or filtering membrane located in the fluid pathway, downstream of the reservoir outlet, and which preferably has a surface oriented transversely in the pathway and the area of which could be in the range approximately between 0.25 and 5 $cm^2$ as far as micro-devices are concerned.

The filter could be arranged to block the nucleation seeds by size exclusion with pore sizes comprised between 10 and 20 nm, for instance, which has been reported to correspond substantially to the typical diameter of an insulin fibril seed. However, the use of such pore sizes may represent an important drawback for the delivery device by introducing a high fluidic resistance in the pathway which may interfere with the flow characteristics of the device during its implementation.

Indeed, with for a same surface and a same porosity ratio, a filter having a pore size of 20 nm exhibits a fluidic resistance which is 120 times higher than a filter having a pore size of 220 nm, which may allow ensuring an aseptic drug infusion through filtration, in principle.

Accordingly, in a preferred embodiment, the membrane may comprise pores of larger sizes so as to perform a blockage of the nucleation seeds by their adsorption on the filtration module surface by the way of hydrophobic interaction.

The Applicant has observed, through experimentations, that the filtering membrane may preferably have a surface with good hydrophobic properties to promote nucleation seeds adsorption and an area large enough to prevent surface nucleation seed saturation. Furthermore, the porosity of the membrane should be chosen so as to allow an effective surface contact to promote the nucleation seed adsorption.

Those experimentations led the Applicant to define general preferred parameters for the filtering membrane which are as follows: it may have a mean pore size that is either approximately X times the mean diameter of the nucleation seeds, where X is equal to 0.9, or smaller, in order to retain the nucleation seeds essentially by size screening, or approximately X times the mean diameter of said nucleus seeds, where X is equal to 2, or larger, in order to retain said nucleation seeds essentially by adsorption on the surface of the pores.

More particularly, the porous membrane may have a mean pore size in the range between 4 and 25 nm, for size screening or, alternately in the range between 50 and 1000 nm for filtration by adsorption.

It may advantageously be made of a material such as micro-structured plastic, for instance taken from the group comprising: Polypropylene (PP), Polystyrene (PS), High impact polystyrene (HIPS), Acrylonitrile butadiene styrene (ABS), Polyethylene terephthalate (PET), Polyester (PES), Polyamides (PA) (Nylons), Poly(vinyl chloride) (PVC), Polyurethanes (PU), Polycarbonate (PC), Polyvinylidene chloride (PVDC), Polyethylene (PE), Polycarbonate/Acrylonitrile Butadiene Styrene (PC/ABS), Polymethyl methacrylate (PMMA), Polytetrafluoroethylene (PTFE), Polyetheretherketone (PEEK), Polyetherimide (PEI), Phenolics (PF), Urea-formaldehyde (UF), Melamine formaldehyde (MF), Polylactic acid and Plastarch material. The membrane may preferably exhibit a porosity in the range between 5 and 50%, while its thickness may be in the range between 5 and 1000 μm.

More particularly and as a non-limiting example, experimentations carried out with a polycarbonate membrane having an area of 1.17 $cm^2$ and a mean pore size of 350 nm led to an increase of nearly 13% of the lag time value which corresponds to the length of time it takes to form the fibril nucleus, as already mentioned. The lag time has been measured, without optimization of the experimental conditions (flow rate, initial fibril seed level), according to the methodology described by L. Nielsen, R. Khurana, A. Coats et al. in "Effect of Environmental Factors on the Kinetics of Insulin Fibril Formation: Elucidation of the Molecular Mechanism.", Biochemistry vol. 40 (2001), pages 6036 to 6046. It can further be noted that the Applicant has observed that an increase of the membrane surface area tended to increase the lag time.

Figure 2A:
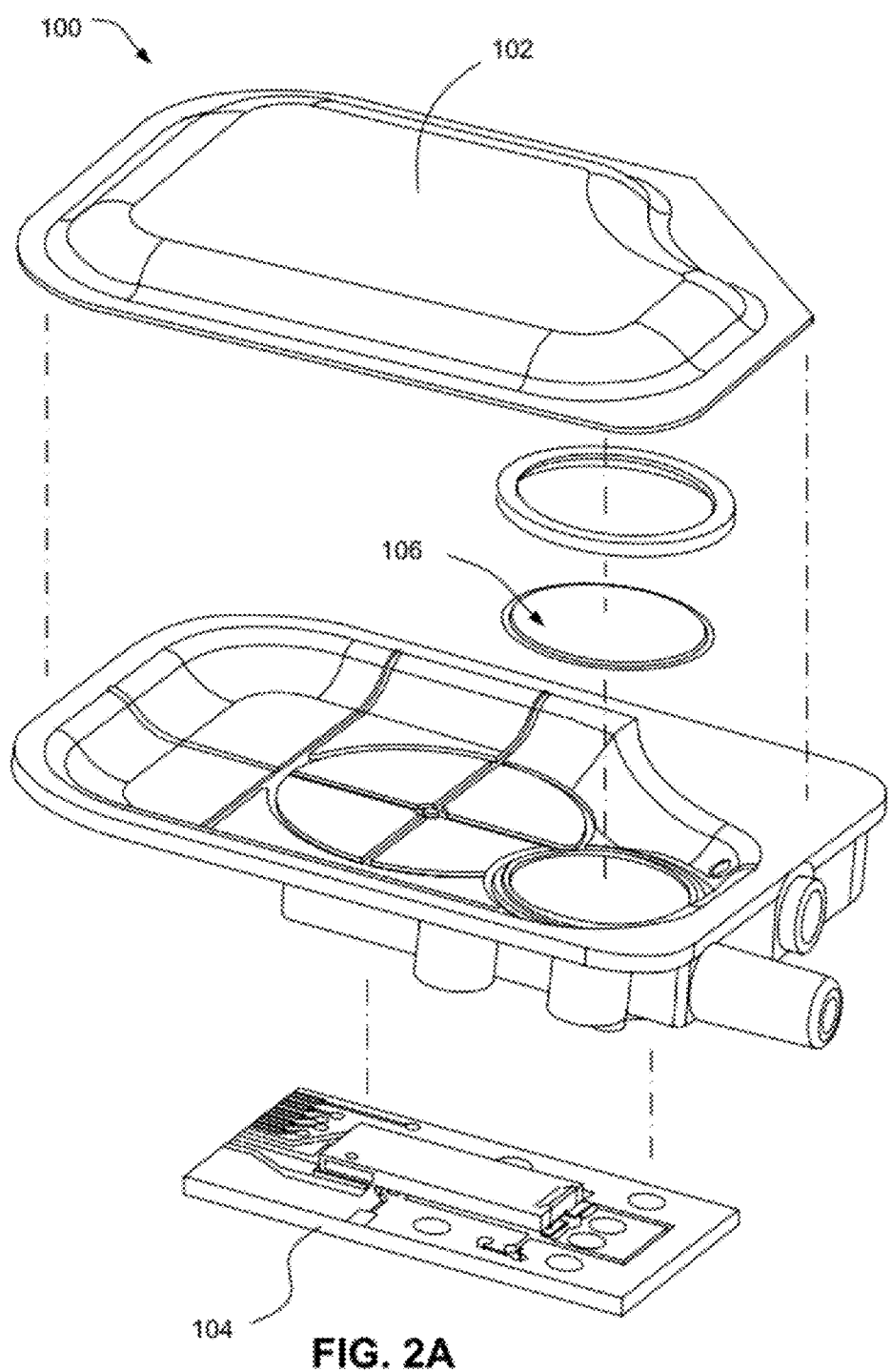
FIG. 2 shows a simplified exploded view of a preferred exemplary embodiment of a drug delivery device according to the present invention.
Figure 2B:
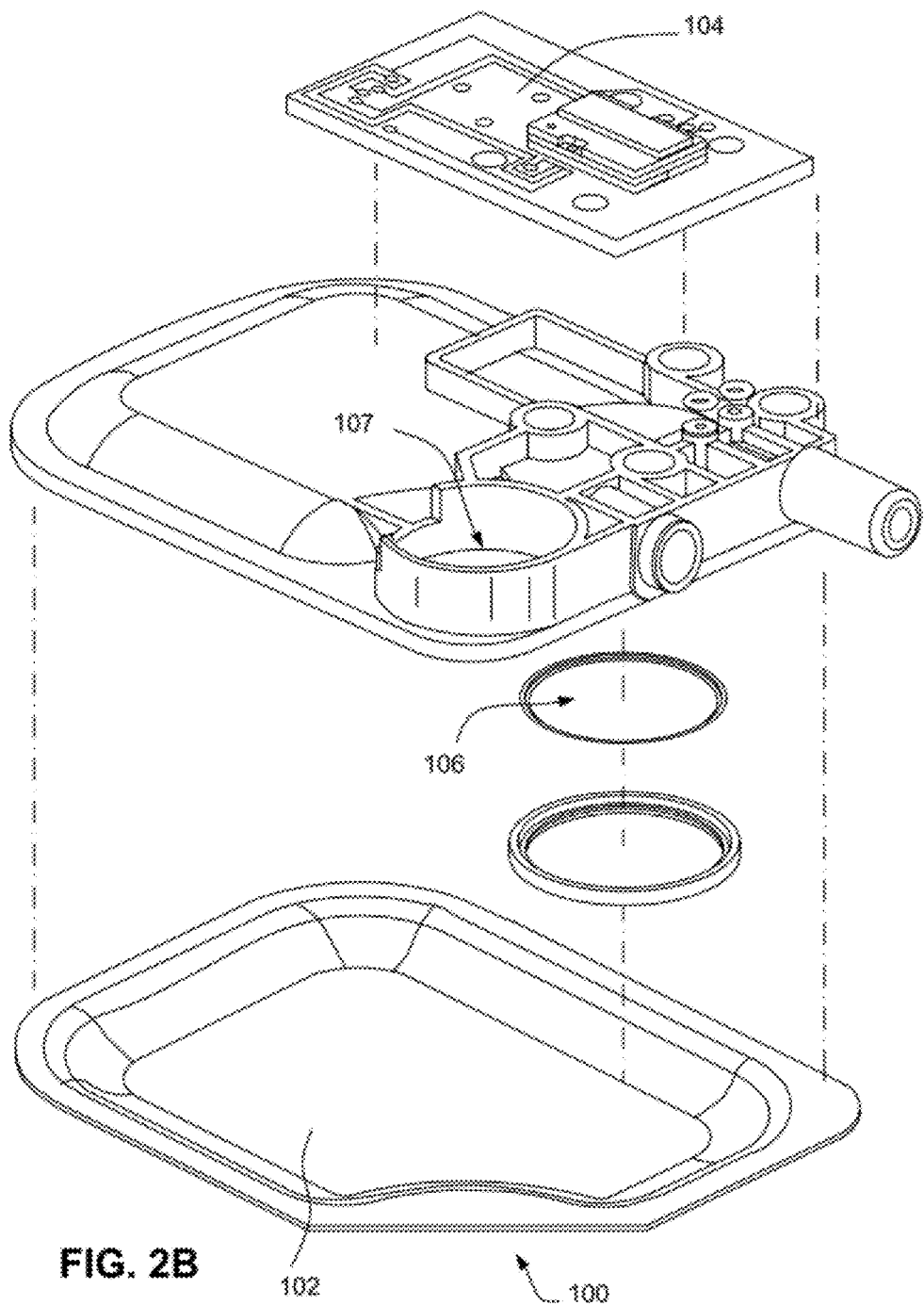

FIG. 2 shows a simplified exploded view of a preferred exemplary embodiment of a drug delivery device according to the present invention.

The device 100 comprises a reservoir 102 and a pump cell 104, while a porous membrane 106 is arranged at the outlet 107 of the reservoir in order to protect the pump cell and the patient from the risk of fibril agglomeration.

It should be noted that the membrane may be arranged at any place along the fluid pathway. However, the reservoir outlet is preferred as far as an arrangement of the membrane at this location allows protecting the pump cell from occlusion together with the other parts of the delivery device.

The smaller the device and its tubing, the more relevant becomes the filtration module according to the invention. Indeed, aggregation can proceed to the extent that a visible precipitate is formed which, obviously, may occlude the device tubing downstream of the reservoir, particularly when it is of small dimensions.

A filter may be provided to prevent air bubbles going out from the reservoir downstream in the pathway. The one skilled in the art will encounter no particular difficulty to optimize one single membrane to filter both air bubbles and nucleation seeds or, alternately, to use two distinct membranes, according to his needs and without departing from the scope of the invention. Indeed, independent of the filtration type, either size screening or adsorption, the filtration module may exhibit hydrophilic surface properties, at least at its external surface arranged on the reservoir side, so as to prevent air bubbles to travel in the pathway, outside the reservoir.

Figure 3:
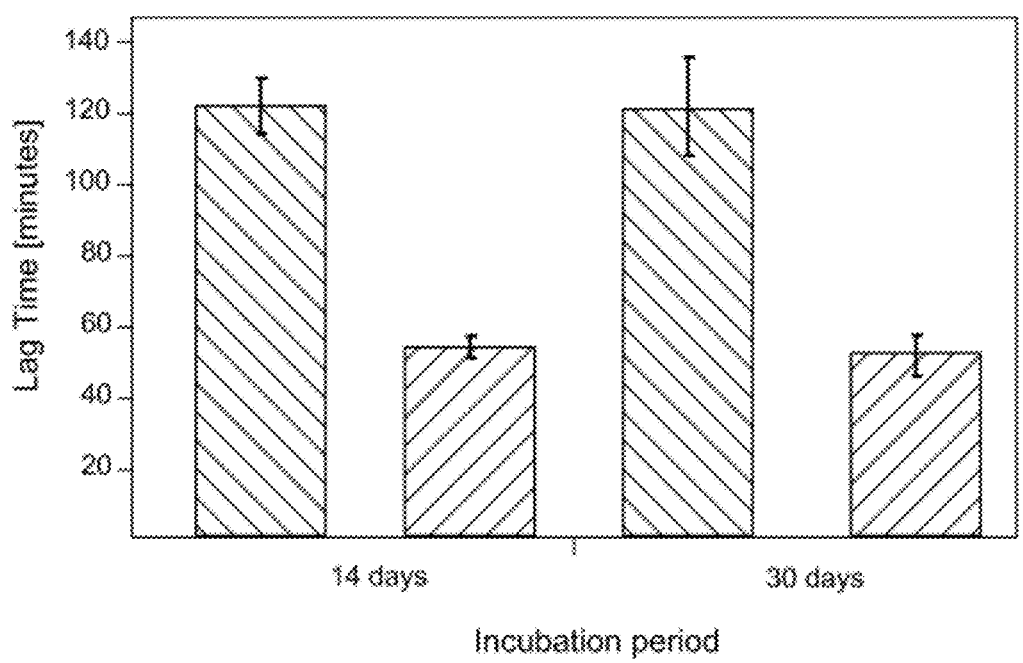
FIG. 3 shows an experimental diagram on which the advantages of the present invention are made apparent.

FIG. 3 shows a diagram of the results of comparative experimentations conducted on the basis of the device of FIG. 2.

More precisely, this diagram shows the lag time as a function of incubation duration (14 and 30 days) of insulin solution of the same batch incubated in the pump reservoir (described in connection with FIG. 2) at 37° C. under orbital agitation. The bar with horizontal strips represent the data of the solution that passed through the filter membrane before analysis, and the bar with the diagonal strips represent the same solution stored in the reservoir and not processed though the filter before analysis. The represented values are the average of 8 measurements and the error bars are the standard deviation. This diagram shows a clear improvement of the lag time thanks to the filter according to the present invention.

The above description corresponds to a preferred embodiment of the invention described by way of non-limiting example. In particular, the forms shown and described for the various component parts of the drug delivery device are not limiting.

The invention claimed is:

1. A drug delivery device for the delivery of a drug fluid comprising drug molecules tending to spontaneously form nucleation seeds leading to fibrils or aggregates, wherein the drug delivery device comprises:
a drug reservoir having a reservoir outlet;
a fluid flow controlling system; and
a fluid pathway in communication with the drug reservoir and extending through the fluid flow controlling system, wherein
the fluid pathway includes a filtration module comprising a porous membrane adapted to absorb nucleation seeds by adsorption, the membrane having hydrophobic properties to promote nucleation seed adsorption and hydrophilic properties to prevent air bubbles from travelling in the fluid pathway.

2. The drug delivery device according to claim 1, wherein said seeds are insulin seeds.

3. The drug delivery device according to claim 1, wherein the pores of the porous membrane are of a sufficiently small size to prevent particles to be transported thereacross.

4. The drug delivery device according to claim 3, wherein said particles have a diameter size which is above 0.45 microns.

5. The drug delivery device according to claim 1, wherein the filtration module is positioned at the drug reservoir outlet.

6. The drug delivery device according to claim 1, wherein the porous membrane has a mean pore size that is approximately X times a mean diameter of said nucleation seeds, where X is equal to 0.9, or smaller, in order to retain said nucleation seeds essentially by size screening.

7. The drug delivery device according to claim 6, wherein the porous membrane has a mean pore size that is substantially in the range between 4 and 25 nm.

8. The drug delivery device according to claim 1, wherein the drug molecules include insulin or any other drug having physicochemical properties similar to insulin.

9. The drug delivery device according to claim 1, wherein the porous membrane has a mean pore size that is approximately X times a mean diameter of the nucleation seeds, where X is equal to 2, or larger, in order to retain said nucleation seeds essentially by adsorption on the pore surfaces.

10. The drug delivery device according to claim 9, wherein the porous membrane has a mean pore size that is substantially in the range between 50 and 1000 nm.

11. The drug delivery device according to claim 9, wherein the drug molecules include insulin or any other drug having physicochemical properties similar to insulin.

12. The drug delivery device according to claim 1 or 11, wherein the porous membrane exhibits the hydrophilic properties at an external surface arranged on a side facing the drug reservoir, and wherein the membrane exhibits the hydrophobic properties within the porous membrane.

13. The drug delivery device according to claim 1, wherein the porous membrane is made of at least one material selected from the group consisting of Polypropylene (PP), Polystyrene (PS), High impact polystyrene (HIPS), Acrylonitrile butadiene styrene (ABS), Polyethylene terephthalate (PET), Polyester (PES), Polyamides (PA) (Nylons), Poly(vinyl chloride) (PVC), Polyurethanes (PU), Polycarbonate (PC), Polyvinylidene chloride (PVDC), Polyethylene (PE), Polycarbonate/Acrylonitrile Butadiene Styrene (PC/ABS), Polymethyl methacrylate (PMMA), Polytetrafluoroethylene (PTFE), Polyetheretherketone (PEEK), Polyetherimide (PEI), Phenolics (PF), Urea-formaldehyde (UF), Melamine formaldehyde (MF), Polylactic acid and Plastarch material.

14. The drug delivery device according to claim 1, wherein the porous membrane has a porosity in a range between 5 and 50%.

15. The drug delivery device according to claim 14, wherein the porous membrane has a thickness in a range between 5 and 1000 μm.

16. The drug delivery device according to claim 1, wherein the porous membrane has an effective surface oriented transversely in said pathway, and wherein an area of the effective surface is in a range between about 0.25 and 5 cm$^2$.

17. The drug delivery device according to claim 1, wherein the porous membrane has a disc shape and is arranged before said pathway at the reservoir outlet.

18. The drug delivery device according to claim 1, wherein the filtration module is further suitable for retaining air bubbles which are prevented from being transported across the porous membrane.

* * * * *